(12) United States Patent
Becker

(10) Patent No.: US 11,617,824 B2
(45) Date of Patent: *Apr. 4, 2023

(54) LUER TO LUER TISSUE MORSELIZER

(71) Applicant: Hilton Becker, Boca Raton, FL (US)

(72) Inventor: Hilton Becker, Boca Raton, FL (US)

( * ) Notice: Subject to any disclaimer, the term of this patent is extended or adjusted under 35 U.S.C. 154(b) by 757 days.

This patent is subject to a terminal disclaimer.

(21) Appl. No.: 16/596,094

(22) Filed: Oct. 8, 2019

(65) Prior Publication Data

US 2020/0155737 A1 May 21, 2020

Related U.S. Application Data

(63) Continuation-in-part of application No. 16/192,459, filed on Nov. 15, 2018.

(51) Int. Cl.
*A61M 1/00* (2006.01)
*A61M 39/10* (2006.01)
*A61B 17/00* (2006.01)

(52) U.S. Cl.
CPC ............... *A61M 1/88* (2021.05); *A61B 17/00* (2013.01); *A61M 1/0062* (2013.01); *A61M 39/10* (2013.01); *A61B 2017/00792* (2013.01); *A61B 2017/00969* (2013.01); *A61M 2039/1083* (2013.01); *A61M 2039/1088* (2013.01); *A61M 2202/08* (2013.01)

(58) Field of Classification Search
CPC .......... A61M 39/10; A61M 2039/1033; A61M 2039/1061; A61M 2039/1072; A61M 2039/1077; A61M 2039/1083; A61M 2039/1088; A61M 5/16813; A61M 5/3007; A61M 5/2053; A61M 1/0094; A61M 1/88; A61M 1/0062; A61B 2017/320775; F16K 3/0281

See application file for complete search history.

(56) References Cited

U.S. PATENT DOCUMENTS

2013/0123747 A1* 5/2013 Tremolada ............. A61K 35/35
241/43

* cited by examiner

*Primary Examiner* — Nathan R Price
*Assistant Examiner* — Justin L Zamory
(74) *Attorney, Agent, or Firm* — Jeffrey D. Moy; Weiss & Moy, PC

(57) ABSTRACT

A morselizer has a first end section with an axially and radially hollow luer fitting, a second end section with an axially and radially hollow luer fitting, a housing juxtaposed therebetween, a channel extending axially between the first end section and the second end section and through the housing providing an axial liquid pathway therein, and at least one blade disposed within the housing. Each end of the morselizer is attachable to a structure with a complimentarily sized luer fitting. In an embodiment, the morselizer facilitates atraumatic resizing of material through axial liquid transfer, by transferring material from a first structure attached to the first end section, thence through the channel, where material is resized by the blade, and through the second end section to a second structure attached to the second end section. The resized material may be suitable for injection, such as through a fine needle.

20 Claims, 9 Drawing Sheets

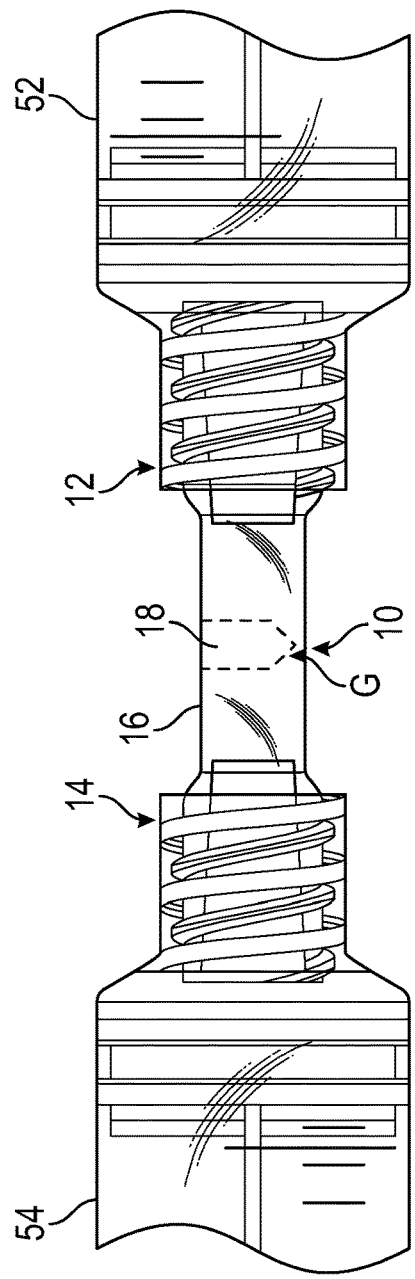
FIG. 5
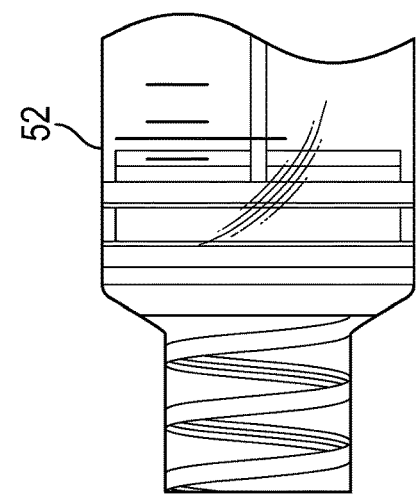
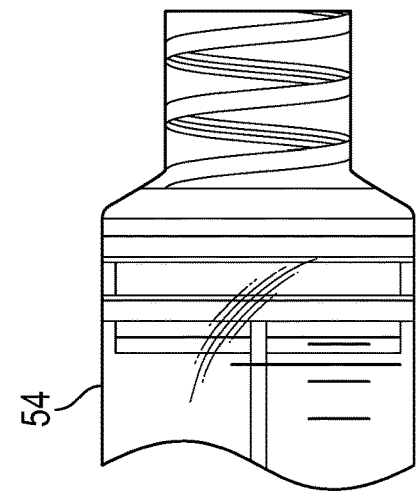
FIG. 6

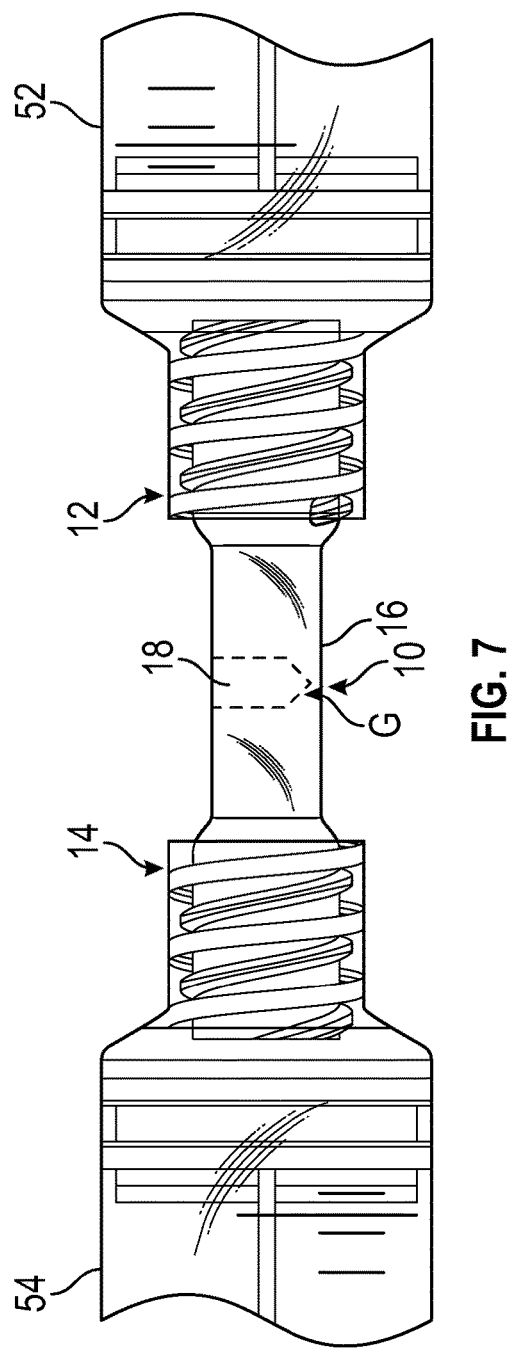
FIG. 7
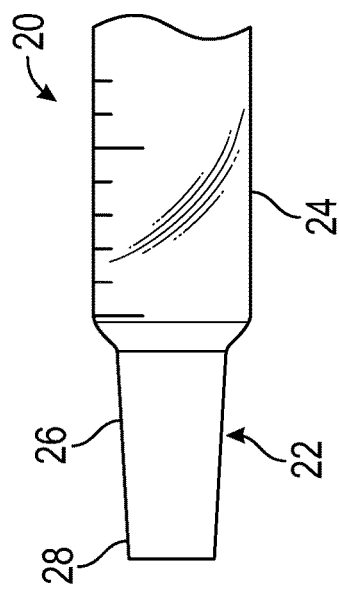
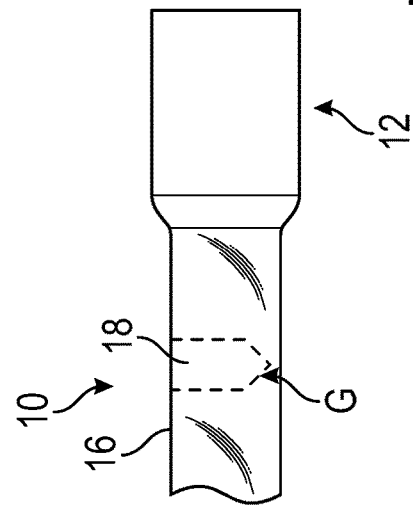
FIG. 8

LUER TO LUER TISSUE MORSELIZER

CROSS-REFERENCE TO RELATED APPLICATION

This application is a continuation-in-part of and claims the benefit of co-pending U.S. application Ser. No. 16/192,459, entitled "LUER TO LUER TISSUE MORSELIZER," which was filed on Nov. 15, 2018 in the name of the inventor, Hilton Becker, herein which claims the benefit of U.S. Provisional Application Ser. No. 62/589,782 filed Nov. 22, 2017, the disclosures of which are hereby incorporated by reference herein in their entirety.

FIELD OF THE INVENTION

The present invention relates to an apparatus with luer or similar fitting for use in atraumatically resizing biologic material.

BACKGROUND OF THE INVENTION

The attachment of a first structure with a male tapered fitting to a second structure with a conforming taper providing a female tapered fitting that is mateable to the first structure male tapered fitting, with a portion of the male tapered fitting of the first structure accommodated within a portion of the female tapered fitting of the second structure, such as the one described in U.S. Pat. No. 5,312,377 to Dalton, is widely used in the medical field to connect two liquid conduits end to end. These so-called luer fittings provide an ISO standardized system (ISO 80369, "Small-Bore Morselizer Standards", referencing ISO 594-1 and ISO 594-2 therein) across small-scale liquid fittings in order to make leak-free connections between two structures, such as a male luer fitting of a structure mateably attachable to a female luer fitting of another structure. These luer fittings are (i) common across medical and laboratory instruments to make leak-free/leakproof, mechanically secure connections between two parts, such as to join hypodermic needles to syringes or one catheter to another catheter; and (ii) described as having a male luer fitting and its mating female luer fitting, with the male luer fitting inserted into the female luer fitting and accommodated therein.

Often, such luer fittings are threaded to allow for a threaded attachment between structures with mateable luer fittings, which is commonly referred to as a "luer lock." Such luer lock fittings are divided into two types called one piece luer lock and two piece luer lock or rotating collar luer lock. The one piece luer lock fitting comes as a single mold, with attachment of a structure with such a fitting to another structure with a conforming luer fitting achieved by rotating the entire fitting. In two piece or rotating collar luer lock, a free rotating threaded collar is assembled to the luer fitting and the attachment of a structure with such a fitting to anther structure with a conforming luer fitting is achieved by rotating the collar. Alternatively, a structure with a luer fitting that is non-threaded can attach to another structure with a conforming luer taper dimension as that of the first structure, with the luer fittings of the conforming structures pressed together, with frictional forces holding the structures together. This is commonly referred to as luer slip or slip tip. The locking luer lock style luer fittings are generally more secure as one structure with an insertive luer (male) fitting is (i) inserted into another structure with a receptive liter (female) fitting and (ii) twisted to form a liter lock attachment, thus preventing accidental separation of the structures in addition to ensuring no liquids can leak through the attachment. Although not having a threaded attachment augmenting the frictional forces between the two attached structures, the luer slip style fitting allows for quicker attachment between two structures with complementarily sized luer fittings as the attachment simply requires a push of the structures together to form the attachment through the frictional forces between the structures.

In the cosmetic and plastic surgery field, fat injections, also known as fat grafting, are performed. Such procedures can be an effective way to reduce wrinkles, diminish acne scarring, and regain a more youthful appearance. By injecting harvested human fat, cosmetic and plastic surgeons can enhance facial fullness, fill deep creases, soften facial creases and wrinkles, plump up lips, and build up shallow contours. In order to be effective, fat particles injected into the face should be no larger than 1 mm in diameter.

The harvesting of fat with a cannula (a thin tube inserted into the fat tissue) is performed as a means of providing fat particles for injection. A common procedure for harvesting fat, also referred to as "lipoharvest," is called the "Coleman technique" and involves a 2 to 3 mm diameter blunt cannula with a luer fitting attached to a 10-mL syringe with a luer fitting.

When injecting fat into a desired area, the diameter of the injection needle should be similar or slightly larger than the cannula opening(s) in, order to avoid damage to the fat particles. In addition, to avoid any unnecessary skin damage when performing fat injection, it is desirable to be able to inject the harvested fat with very narrow-diameter needles, viz., 0.5 to 2.5 mm, to make only small diameter wounds in the skin. However, in order to harvest smaller particles that can pass through such needles, cannulas have been manufactured with smaller holes than traditional cannulas. Although smaller fat particles are obtained, the beneficial fraction comprised of the desirable stromal vascular fraction (SVF) containing a large population of regenerative cells called adipose derived regenerative cells (ADRCs) comprised in part of fibroblasts and stem cells.

As such, it is desirable to harvest larger particles containing the SVF and have a device that allows for atraumatic resizing of the relatively large harvested fat particles without loss of the beneficial SV fraction, while not losing sight of the need for smaller particles to ensure survival until the new blood supply is established to allow for the injection of effectively-sized fat particles viz., no larger than 1 mm).

SUMMARY OF THE INVENTION

A first aspect of the invention comprises a morselizer comprising (a) a hollow cylindrical structure with an inner wall and an outer wall and comprising a first end section, a second end section, and a center section extending axially between the first end section and the second end section providing an axial liquid pathway therein; (b) wherein each end section comprises an axially and radially hollow luer fitting that is attachable to a structure with a complementarily sized luer fitting; and (c) one or more blades extending transversally across the inner diameter of the center section wherein (i) each blade is comprised of a plurality of ends, including a posterior end secured to at least the center wall section inner wall at a center section inner wall first position and an anterior end proximal a center section inner wall second position opposite the center section inner wall first position, with a gap positioned between the blade anterior end and the center section inner wall second position, and (ii) at least two ends comprise cutting ends.

A second aspect of the invention comprises a morselizer comprising (a) a hollow cylindrical structure with an inner wall and an outer wall and comprising a first end section, a second end section, and a center section extending axially between the first end section and the second end section providing an axial liquid pathway therein; (b) wherein each end section comprises an axially and radially hollow luer fitting that is attachable to a structure with a complementarily sized luer fitting; (c) wherein the first end section comprises a threaded male luer fitting with a plurality of threads formed on the first end section outer wall; and (d) one or more blades extending transversally across the inner diameter of the center section wherein (i) each blade is comprised of a plurality of ends, including a posterior end secured to at least the center wall section inner wall at a center section inner wall first position and an anterior end proximal a center section inner wall second position opposite the center section inner wall first position, with a gap positioned between the blade anterior end and the center section inner wall second position, and (ii) at least two ends comprise cutting ends.

A third aspect of the invention comprises a morselizer comprising (a) a hollow cylindrical structure with an inner wall and an outer wall and comprising a first end section, a second end section, and a center section extending axially between the first end section and the second end section providing an axial liquid pathway therein; (b) wherein each end section comprises an axially and radially hollow luer fitting that is attachable to a structure with a complementarily sized luer fitting; (c) wherein the first end section comprises a threaded female luer fitting with a plurality of threads formed on the first end section inner wall; and (d) one or more blades extending transversally across the inner diameter of the c section wherein (i) each blade is comprised of a plurality of ends including a posterior end secured to at least the center wall section inner wall at a center section inner wall first position and an anterior end proximal center section inner wall second position opposite the center section inner wall first position, with a gap positioned between the blade anterior end and the center section inner wall second position, and (ii) at least two end comprise cutting ends.

A fourth aspect of the invent comprises a morselizer comprising (a) a hollow cylindrical structure with an inner wall and an outer wall and comprising a end section, a second end section, and a center section extending axially between the first end section and the second end section providing an axial liquid pathway therein; (b) wherein each end section comprises an axially and radially hollow luer fitting that is attachable to a structure with a complementarily sized luer fitting; (c) wherein the first end section comprises a threaded female-male-luer fitting with a plurality of threads formed on the first end section inner wall and the first end section outer wall; and (d) one or more blades extending transversally across the inner diameter of the center section wherein (i) each blade is comprised of a plurality of ends, including a posterior end secured to at least the center wall section inner wall at a center section inner wall first position and an anterior end proximal a center section inner wall second position opposite the center section inner wall first position, with a gap positioned between the blade anterior end and the center section inner wall second position, and (ii) at least two ends comprise cutting ends.

A fifth aspect f the invention comprises a morselizer comprising, in combination: a first end section, wherein the first end section comprises an axially and radially hollow luer fitting attachable to a structure with a complimentarily sized luer fitting; a second end section, herein the second end section comprises an axially and radially hollow luer fitting that is attachable to a structure with a complimentarily sized luer fitting; a housing juxtaposed between the first end section and the second end section, wherein the housing comprises a first housing section and a section housing section, wherein the first housing section and second housing section are configured to be coupled together to form the housing; a channel extending axially between the first end section and the second end section and through the housing providing an axial liquid pathway therein; and at least one blade disposed within the housing and extending transversally across an inner diameter of the channel, wherein the at least one blade comprises a plurality of ends, including a posterior end, an anterior end, and at least two side ends, wherein the at least two side ends comprise cutting ends.

A sixth aspect of the invention comprises a morselizer comprising, in combination: a first end section, wherein the first end section comprises an axially and radially hollow luer fitting that is attachable to a structure complimentarily sized luer fitting; wherein the first end section comprises a shoulder, the shoulder including threading thereon; a second end section, wherein the second end section comprises an axially and radially hollow luer fitting that is attachable to a structure with a complimentarily sized luer fitting; wherein the second end section comprises a shoulder, the shoulder including threading thereon; a housing juxtaposed between the first end section and the second end section, wherein the housing comprises a first housing section and a section housing section, wherein the first housing section and second housing section are configured to be coupled together to form the housing; wherein the first housing section and the second housing section each include at least one blade support; a channel extending axially between the first end section and the second end section and through the housing providing an axial liquid pathway therein; and at least one blade disposed within the housing and extending transversally across an inner diameter of the channel, wherein the at least one blade comprises a plurality of ends, including a posterior end, an anterior end, and at least two side ends, wherein the at least two side ends comprise cutting ends.

A seventh aspect of the invention comprises morselizer comprising, in combination: a first end section, wherein the first end section comprises an axially and radially hollow luer fitting that is attachable to a structure with a complimentarily sized luer fitting; wherein the first end section comprises a shoulder, the shoulder including threading thereon; a second end section, wherein the second end section comprises an axially and radially hollow luer fitting that is attachable to a structure with a complimentarily sized luer fitting; wherein the second end section comprises a shoulder, the shoulder including threading thereon; a housing juxtaposed between the first end section and the second, end section, wherein the housing comprises: a first housing section, wherein the first housing section comprises at least one depression region and at least one receptacle; and a section housing section, wherein the second housing comprises at least one retaining wall and at least one peg; wherein the first housing section and second housing section are configured to be coupled together to form the housing, wherein the at least one depression region is configured to receive a portion of the at least one retaining wall and the at least one receptacle is configured to receive the at least one peg; wherein the first housing section and the second housing section each include at least one blade support; a channel extending axially between the first end section and the second end section and through the housing providing an axial liquid pathway therein; and at least one blade disposed within the housing and extending transversally across an inner diameter of the channel, wherein the at least blade comprises a plurality of ends, including a posterior end an anterior end, and at least two side ends, wherein the at least two side ends comprise cutting ends.

In an embodiment, the morselizer allows for a traumatic resizing of material through the morselizer by (I) attaching a first structure with a luer fitting containing fat tissue with its collagen supporting structure (SVF) in a substantially liquid solution to the morselizer by attaching the first structure luer fitting to the luer fitting at the first end section of the morselizer and attaching a second structure with a luer fitting to the luer fitting at the second end of the morselizer; and (II) transferring the solution from the first structure to the morselizer through the first structure-morselizer luer fitting attachment, thence through the morselizer center section where material is resized by the one or more blades positioned in the morselizer center section and through the second end section of the morselizer to the second structure through the second structure-morselizer luer fitting attachment; and, as needed or desired by the user, (III) successively transferring solution from the second structure through the morselizer to the first structure and thence back to the second structure through the morselizer as discussed above at (II).

In another embodiment, the morselizer allows for atraumatic resizing of material through the morselizer by (I) attaching a first structure with a luer fitting containing fat tissue with its collagen supporting structure (SVF) in a substantially liquid solution to the morselizer by attaching the first structure luer fitting to the luer fitting at the first end section of the morselizer and attaching a second structure with a luer fitting to the luer fitting at the second end of the morselizer; and (II) transferring the solution from the first structure to the morselizer through the first structure-morselizer luer fitting attachment, thence through the morselizer housing where material is resized by the one or more blades positioned in the morselizer housing and through the second end section of the morselizer to the second structure through the second structure-morselizer luer fitting attachment; and, as needed or desired by the user, (III) successively transferring solution from the second structure through the morselizer to the first structure and thence back to the second structure through the morselizer as discussed above at (II).

Although the invention described herein is done so in the context of fat harvesting for injection into the body, the invention is useable in any medical or other scientific procedure wherein substantially solid material, such as particles of a larger size, are atraumatically resized to a smaller desired size.

Further additional, advantageous aspects of the invention, such as variants of the aspects of the invention disclosed above, will become apparent to one of ordinary skill in the art upon review of the following description of the embodiments of the invention and the claims and with reference to the accompanying drawings.

By way of example only, specific embodiments of the invention will now be described, with reference to the accompanying drawings, in which:

DESCRIPTION OF THE DRAWINGS

FIG. 5 is side elevation view of an embodiment of the present invention attached to a plurality of structures, each with a luer fitting;

FIG. 6 is a side elevation view of an embodiment of the present invention spaced apart from a plurality of structures, each with a luer fitting;

FIG. 7 is side elevation view of an embodiment of the present invention attached to a plurality of structures, each with a luer fitting;

FIG. 8 is a partial side elevation view of an embodiment of the present invention spaced apart from a structure with a luer fitting;

DETAILED DESCRIPTION OF THE INVENTION

Figure 1:
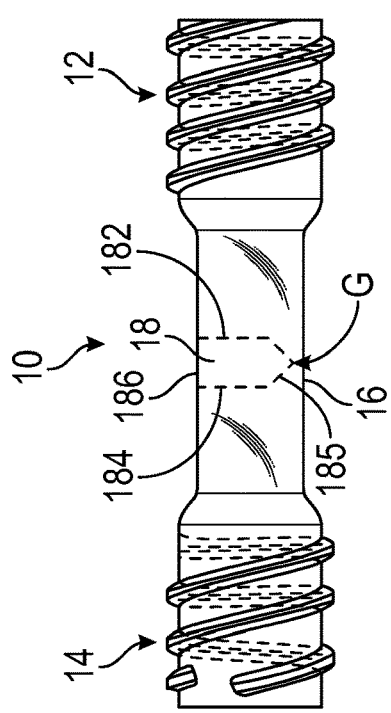
FIG. 1 is a side elevation view of an embodiment of the present invention.

Referring to FIGS. 1-9, morselizer 10 comprises a hollow structure, preferably a thin-walled cylinder, with an inner wall I and an outer wall O and extending axially from a first end and a second end (i.e., the cylinder flat surfaces or bases), wherein both ends are open. Morselizer 10 can be made of any one or more materials known in the art, such as glass, preferably laboratory-grade glass; metal; or plastic, preferably a plastic impervious to and non-degraded by aqueous and organic solutions.

With reference to FIGS. 1-7, morselizer 10 is comprised of first end section 12, second end section 14, and center section 16 extending axially between first et d section 12 and second end section 14. The axis of morselizer 10 provides an axial liquid pathway along the hollow structure thereof, extending from first end section 12 to center section 16 and then to second end section 14. Preferably, the inner diameter of morselizer 10 is axially continuous, with the inner diameters of each of first end section 12, second end section 14, and center section 16 the same. Morselizer 10 can have an inner diameter of any size capable of being complementarily sized to structures with small-scale liquid fittings, preferably in the range of 0.1 mm to 10 mm, more preferably in the range of 2 to 5 mm, most preferably in the range of 3 to 4 mm, with an outward bevel extending from center section 16 to first end section 12 and second end section 14.

With reference to FIGS. 1-7, each end section 12/14 of morselizer 10 comprises an axially and radially hollow luer fitting that is attachable to a structure with a complementarily sized luer fitting. The attachment of the morselizer 10 at each of the end sections 12 and 14 comprising a luer fitting to a structure containing a substantially liquid solution with substantially solid materials suspended therein and having a complementarily sized luer fitting prevents any solution leakage out of the structure during material flow from the structure to morselizer 10. The structure with a complementarily sized luer fitting and attachable to the morselizer 10 at each of the end sections 12/14 can comprise any structure with a luer fitting or luer-compatible fitting (such as a non-luer fitting to luer fitting adapter or other luer to non-luer adaptive structure), such as laboratory glassware, plasticware, or metalware, including, by way of example only and not of limitation, vials, tubes (boiling, test, Thiele), luer lock tip or luer slip tip syringes, burettes, pipettes, cylinders, flasks, beakers, funnel, distilling columns, chromatography columns or other columns used in analytical techniques, or condensers.

The luer fittings comprising end sections 12/14 can be characterized as either (i) "male", with the luer fitting on end section 12/14 of morselizer 10 accommodated within another structure with a luer fitting when the structure is attached to the morselizer 10; or (ii) "female", with the luer fitting on end section 12/14 of morselizer 10 accommodating therein another structure with a luer fitting when the structure is attached to the morselizer 10. Moreover, morselizer end section 12/14 comprising a luer fitting can be threaded or unthreaded, with such threaded or unthreaded morselizer end section 12/14 attachable to a complementarily sized unthreaded or threaded luer fitting on a structure, with (i) the threaded mating and frictional forces generated between the structure and morselizer 10 maintaining the attachment of a threaded morselizer end section 12/14 to a threaded structure and (ii) frictional forces alone maintaining the morselizer-structure attachment in the absence of a mating of threads between the morselizer end section 12/14 and the structure fitting.

With reference to FIGS. 1-7, in an embodiment of the invention, formed on an inner wall (female) (FIGS. 2-3), outer wall (male) (FIGS. 1, 4-7), or both outer and inner walls (male-female, not depicted) of morselizer end section 12/14 comprising a luer fitting are a plurality of threads to allow for a threaded attachment of the end section 12/14 of morselizer 10 to a structure with a complementarily sized threaded or unthreaded luer fitting. In an embodiment of the invention, a threaded luer fitting of end section 12/14 of morselizer 10 is attachable to a structure with a complementarily sized unthreaded luer fitting such as the fitting. In another embodiment of the invention and with reference to FIG. 8, one or more of end sections 12 and 14 (shown as end section 12 in FIG. 8) comprises a threaded luer fitting that is attachable to a structure 20 with a complementarily sized unthreaded luer fitting 28 by pressing the morselizer 10 and structure 20 together so as to form a luer slip attachment between the morselizer end section and the structure luer fitting, with the attachment of a morselizer end section 12/14 comprising a threaded luer fitting to a complementarily sized unthreaded liter fitting on a structure effectuated from frictional forces generated between the structure and morselizer 10.

Figure 2:
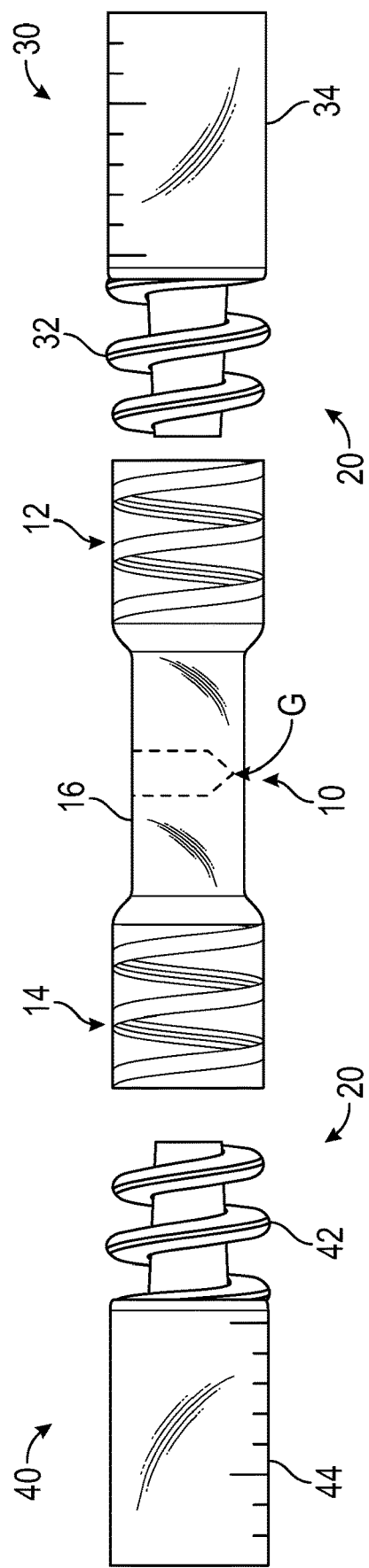
FIG. 2 is a side elevation view of an embodiment of the present invention spaced apart from a plurality of structures, each with a luer fitting.
Figure 3:
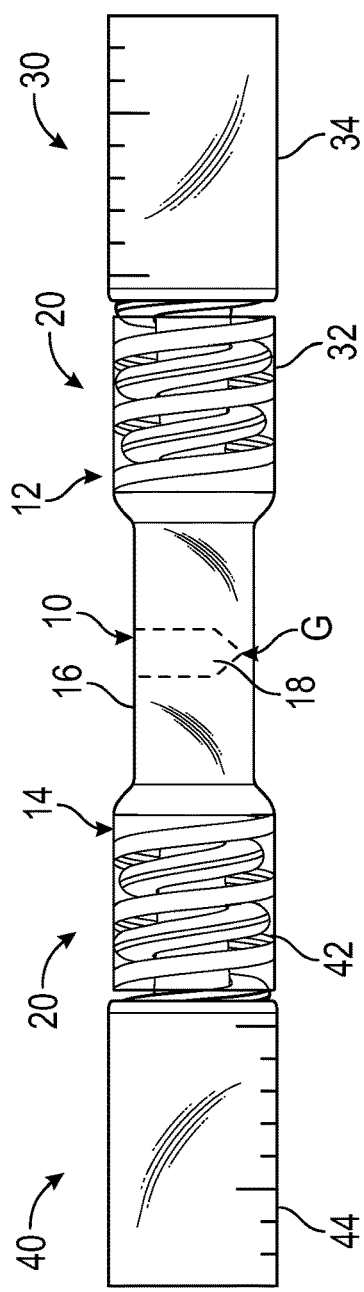
FIG. 3 is a side elevation view of an embodiment of the present invention attached to a plurality of structures, each with a luer fitting.

In an embodiment of the invention and with reference to FIGS. 1-3, one or more of end sections 12 and 14 of morselizer 10 comprises a female luer fitting wherein the inner wall of such end sections 12/14 has disposed thereon a plurality of threads so as to threadedly attach such morselizer end section 12/14 to a structure (30 or 40 as shown in FIGS. 2-3) with a complementarily sized male luer fitting with a plurality of threads formed on the outer wall of such structure (32 or 42, as shown in FIGS. 2-3), such plurality of threads mateable to the plurality of threads of morselizer end section 12/14, with the female luer fitting end section 12/14 securely accommodating therein the male luer fitting (32 or 42 as shown in FIGS. 2-3) of the mateable structure (30 or 40 as shown in FIGS. 2-3).

In an embodiment of the invention, each end section 12 and 14 of morselizer 10 comprises a threaded female luer fitting and can be attached to, a structure with a complementarily sized threaded male luer fitting. With reference to FIGS. 2-3, each of first end section 12 and second end section 14 of morselizer 10 comprises an axially and radially hollow female luer fitting with an inner wall having a plurality of threads disposed thereon so as to allow for a threaded attachment of (i) morselizer 10 at first end section 12 to a first structure 30 at the first structure threaded luer fitting 32, with the first structure threaded luer fitting 32 accommodated within the morselizer first end section 12, and (ii) morselizer 10 at second end section 14 to a second structure 40 at the second structure threaded luer fitting 42, with the second structure threaded luer fitting 42 accommodated within the morselizer second end section 14.

In another embodiment of the invention, a female threaded luer fitting end section 12/14 as that described above is attachable to a structure with an unthreaded complementarily sized male luer fitting (such as luer fitting 28 on lure 20 in FIG. 8) by pressing the morselizer 10 and the attachable structure together (not depicted) forming a luer slip attachment between the morselizer 10 and the structure.

In another embodiment of the invention, formed on the outer wall of a female threaded luer fitting end section 12/14 is a plurality of threads so as to render end section 12/14 a male-female luer fitting which could alternatively threadedly accommodate in the interior of end section 12/14 a male threaded luer fitting of a structure or be threadedly accommodated within a female threaded luer fitting of a structure (not depicted).

In an embodiment of the invention and with reference to FIGS. 4-7, one or more of end sections 12 and 14 of morselizer 10 comprises a male luer fitting wherein the outer wall of such end sections 12/14 has disposed thereon a plurality of threads so as to threadedly attach such morselizer end section 12/14 to a structure, such as structure 52/54 as shown in FIGS. 4-7, with a complementarily sized female luer fitting with a plurality of threads formed on the inner wall of such structure 52/54 as shown in FIGS. 4-7, such plurality of threads mateable to the plurality of threads of morselizer end section 12/14, with the female luer fitting of the structure 52/54 securely accommodating therein the male luer fitting of morselizer end section 12/14 as shown in FIGS. 4-7.

In an embodiment of the invention, each end section 12 and 14 of morselizer 10 comprises a threaded male luer fitting and can be attached to a structure with a complementarily sized threaded female luer fitting. With reference to FIGS. 4-7, each of first end section 12 and second end section 14 of morselizer 10 comprises an axially and radially hollow male luer fitting with an outer wall having a plurality of threads disposed thereon so as to allow for a threaded attachment of (i) morselizer 10 at first end section 12 to a first structure at the first structure threaded female luer fitting 52, with the male fitting of first end section 12 accommodated within the first structure female luer fitting 52 and (ii) morselizer 10 at second end section 14 to a second structure 40 at the second structure threaded female luer fitting 42, with the male fitting of second end section 14 accommodated within the second structure female luer fitting 42.

In another embodiment of the invention, a male threaded luer fitting end section 12/14 as that described above is attachable to a structure with an unthreaded complementarily sized female luer fitting by pressing the morselizer 10 and the attachable structure together (not depicted).

In another embodiment of the invention, formed on the inner wall of a male threaded luer fitting end section 12/14 is a plurality of threads so as to render end section 12/14 a male-female luer fitting which could alternatively threadedly accommodate a male threaded luer fitting of a structure in the interior of end section 12 or be threadedly accommodated within a female threaded luer fitting of a structure (not depicted).

Figure 9:
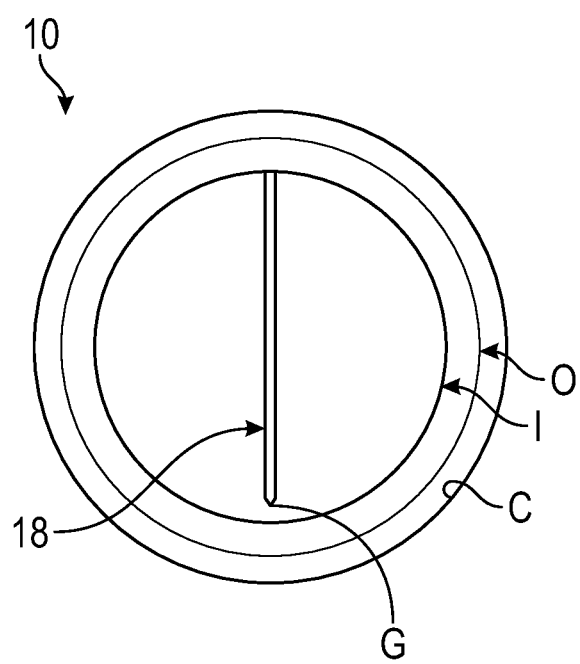
FIG. 9 is a cross-sectional end view of an embodiment of the present invention.

In some embodiments of the invention and with reference to FIG. 9, one or more end sections 12/14 of morselizer 10 has attached to and overlaying the outer wall O of such one or more end sections 12/14 a collar C, with the collar C having an inner wall proximal the outer wall O of morselizer end section 12/14 and having formed thereon a plurality of threads, wherein the collar C is freely rotatable and, when rotated, partially axially displaceable from morselizer outer wall O of morselizer end section 12/14 to allow for a threaded attachment of the collar C to a structure with a complementarily sized threaded luer fitting to form a two piece rotating collar luer lock attachment between morselizer 10 and the structure, with the structure luer fitting accommodated within the inner wall of the collar C.

Figure 4:
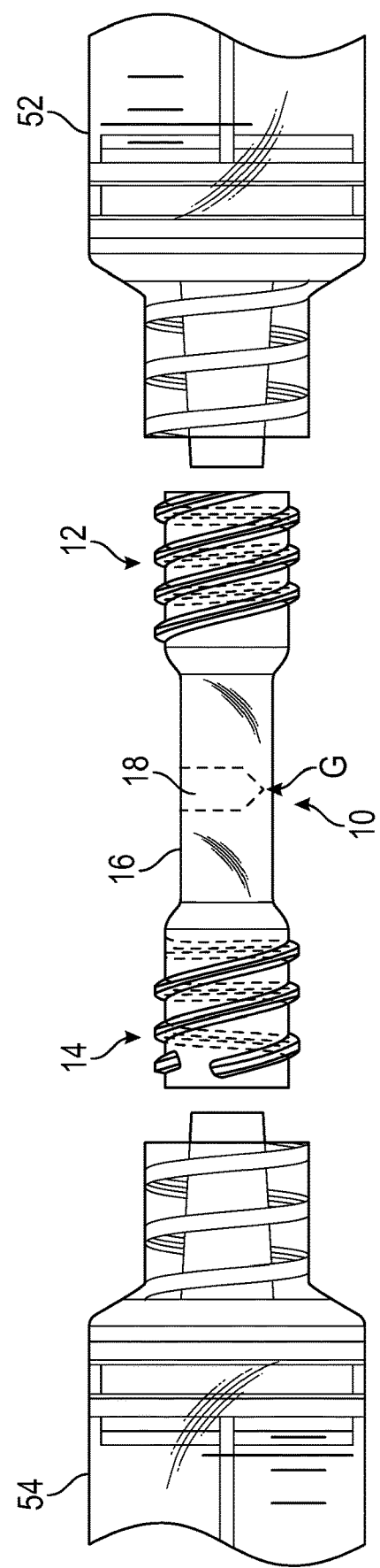
FIG. 4 is a side elevation view of an embodiment of the present invention spaced apart from a plurality of structures, each with a luer fitting.

Often, a structure has a luer fitting comprising an inner hollow core, within which is the liquid flow path, extends and protrudes from an outer hollow sleeve, with the inner core forming a tip, such as the luer fittings 52 and 54 shown in FIGS. 4 and 5, with the inner wall of the sleeve having positioned thereon a plurality of threads. Such a structure, often referred to as a threaded luer lock tip, threaded liter tip, or simply luer tip (such structure hereinafter "luer tip structure"), is attachable to a morselizer end section 12/14 comprising a luer fitting having a plurality of threads formed on the outer wall of such end section 12/14 (male luer fitting), with such end section 12/14 threadedly attached to the luer tip structure 52/54, wherein the plurality of threads of male luer fitting of end section 12/14 are complementarily mateable to the plurality of threads on the inner wall of the sleeve of the luer tip structure luer fitting 52/54, with the end section 12/14 of morselizer 10 (i) accommodating therein the core of the luer tip structure luer fitting 52/54 and (ii) accommodated within the sleeve of the luer tip structure luer fitting 52/54.

In another embodiment of the invention, a morselizer end section 12/14 comprising a luer fitting having a plurality of threads formed on the inner wall of such end section 12/14 is attachable to a structure 52/54 with a liter tip fitting 52/54, with frictional forces between morselizer 10 and the structure 52/54 maintaining the end section 12/14—structure 52/54 attachment.

With reference to FIGS. 1-9, positioned in center section 16 is one or more blades 18, preferably one blade 18. With reference to FIG. 1, each of the one or more blades 18 is a planar structure defined by posterior and anterior ends and at least two side ends wherein at least two ends, preferably the two side ends, comprise cutting ends, such blade 18 comprising (i) a first end 182 proximal first end section 12 and preferably comprising a cutting end, (ii) a posterior end 186 secured to morselizer 10 at center section 16, (iii) a second end 184 proximal second end section 14 and preferably comprising a cutting end, and (iv) an anterior end 185 positioned in the hollow interior of morselizer 10 at center section 16 preferably comprising a cutting end, more preferably ending at a point. Such one or more blades 18 extends transversally from the blade posterior end 186 at a center section inner wall first position across the inner diameter of center section 16 to the blade anterior end 185 to a position short of a center section inner wall second position opposite the center section inner wall first position, leaving a gap G between the blade anterior end 185 and the center section inner wall second position.

In a preferred embodiment, posterior blade end 186 is secured to morselizer 10 inner wall at center section 16 by a glass-to-metal seal. More preferably, posterior blade end 186 extends through morselizer 10 inner wall with a glass-to-metal seal formed in the glass matrix between the inner and outer walls of morselizer 10 at center section 16. Additionally and preferably, the one or more blades 18 are axially positioned toward the axial midpoint of morselizer 10 at center section 16, preferably with at least one of the one or more blades 18 axially positioned at the axial midpoint of morselizer 10 at the center section 16 axial midpoint.

Each of the one or more blades 18 positioned in center section 16 comprises any blade type known in the art. Preferably, at least one of the one or more blades 18 comprises a scalpel blade, more preferably, a double-sided scalpel blade 18 with first end 182 proximal first end section 12 and second end 184 proximal second end section 14 wherein first cutting edge 182 and second cutting edge 184 each extend transversally across center section 16 and taper toward each other forming anterior end 185 and ending at a blade point proximal the inner diameter of center section 16.

The morselizer allows for atraumatic resizing of material through axial transfer through the axial liquid pathway of the morselizer by (I) attaching a first structure with a luer fitting containing material in a liquid solution to the morselizer by attaching the first structure luer fitting to the morselizer luer fitting at the first end section of the morselizer and attaching a second structure with a luer fitting to the morselizer luer fitting at the second end of the morselizer and (II) transferring material in the liquid solution from the first structure to the morselizer through the first structure-morselizer luer fitting attachment, thence through the morselizer center section where material is resized by the one or more blades positioned in the morselizer center section and through the second end section of the morselizer to the second structure through the second structure-morselizer luer fitting attachment; and, as needed or desired by the user depending on the given size of the diameter and the desired size of the diameter, (III) successively transferring material in the liquid solution from the second structure through the morselizer to the first structure and thence back to the second structure through the morselizer as discussed above at (II). The desired size of the atraumatically resized material is determined in large part by the size of the gap G separating the one or more blades 18 and the center section 16 inner wall, with the average diameter of the desired material approximating the size of the gap G.

Referring now to FIGS. 10-13, reference number 200 refers generally to another embodiment of the morselizer of the present invention. Morselizer 200 provides features and benefits similar to morselizer 10 and further provides means that allow for improved centering of the blade within the morselizer, as described further herein. In this embodiment, morselizer 200 generally comprises the following main components: a first end section 210, a second end section 212, and a housing 214 juxtaposed therebetween. Morselizer 200 can be made of any one or more materials known in the art, such as glass, preferably laboratory-grade glass; metal;

or plastic, preferably a plastic impervious to and non-degraded by aqueous and organic solutions, and can be injection-molded.

Figure 10:
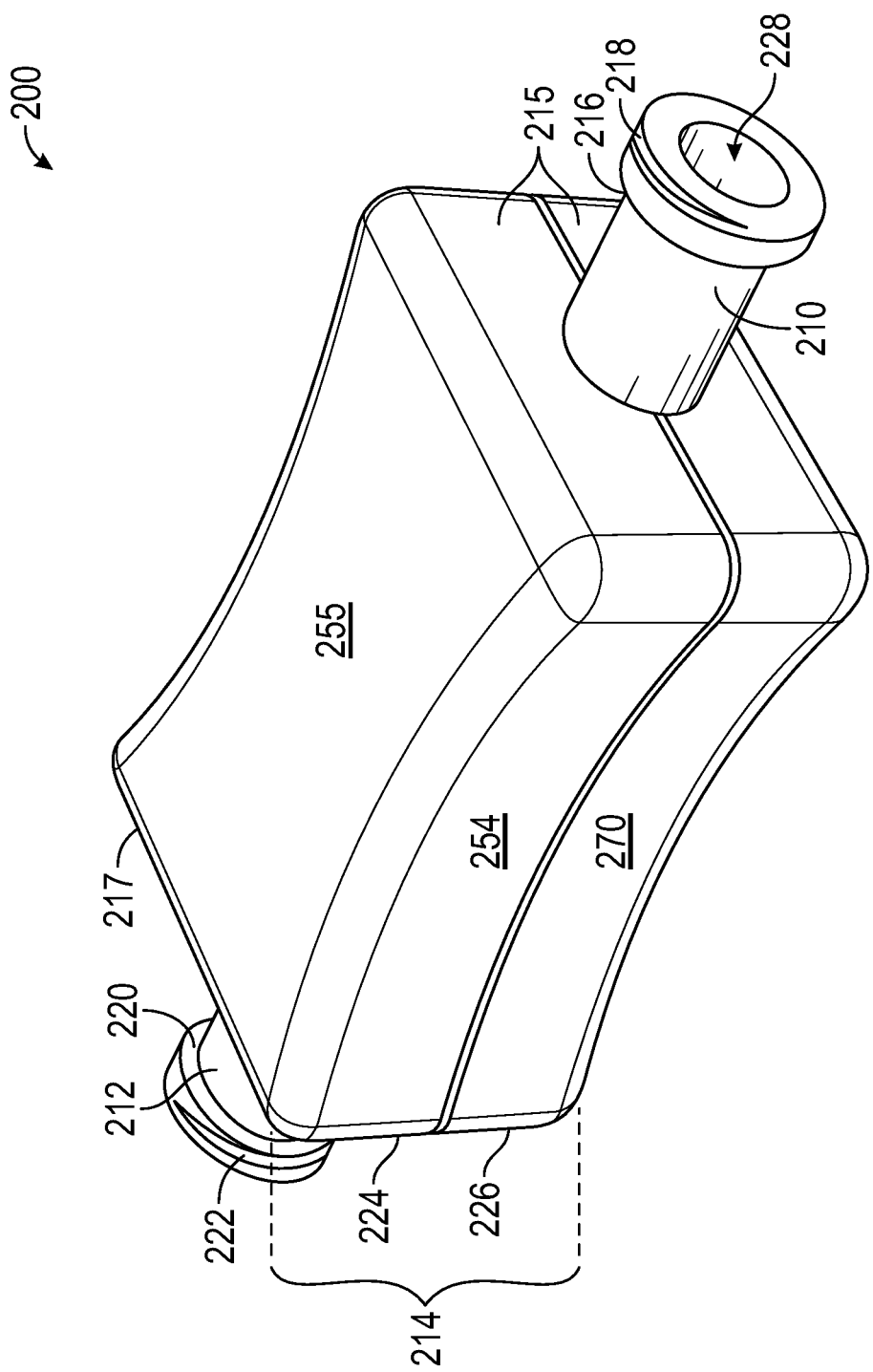
FIG. 10 is a perspective view of another embodiment of the present invention.
Figure 11:
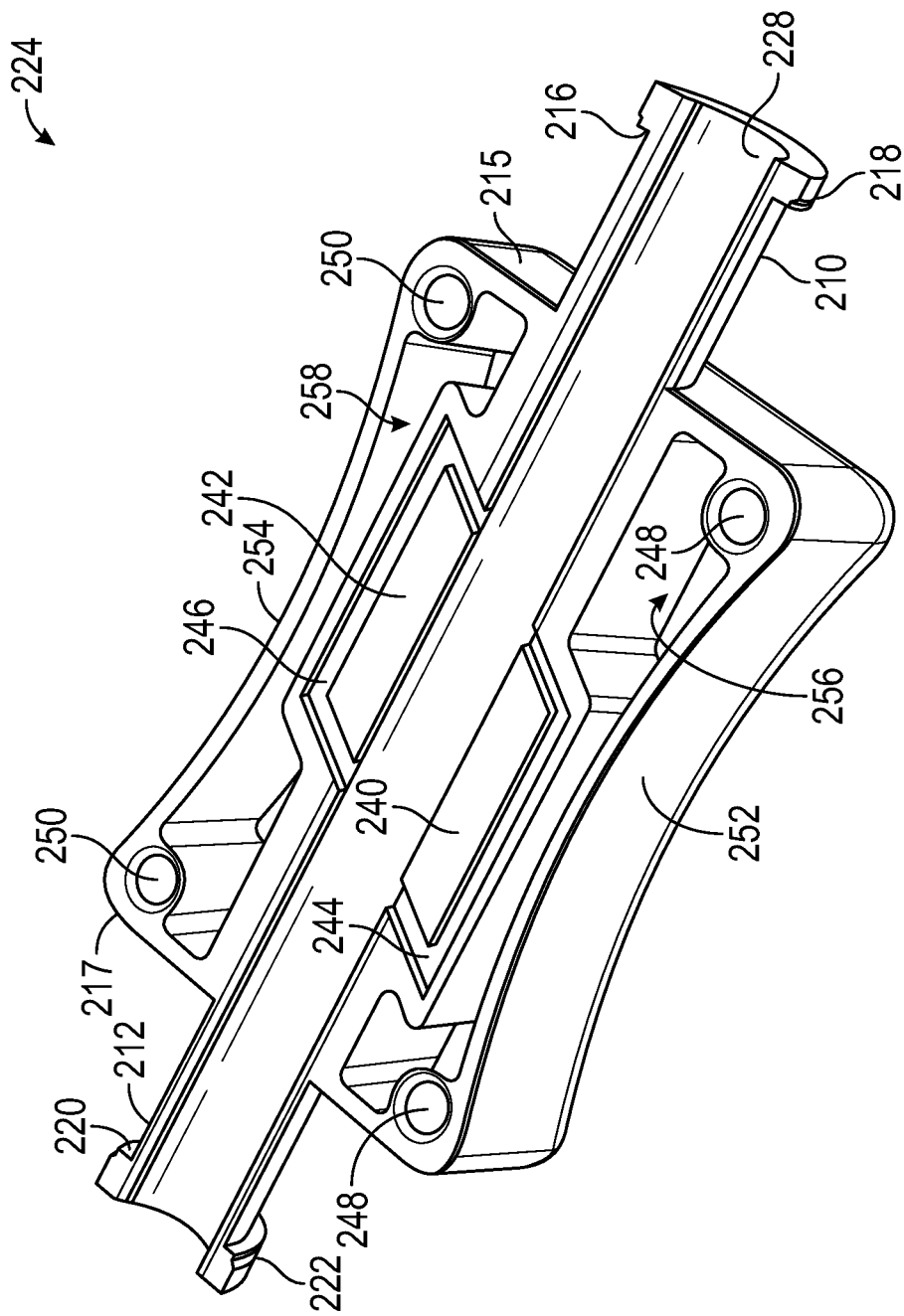
FIG. 11 is a cross-sectional view of the embodiment of FIG. 10, illustrating a first housing section thereof.
Figure 12:
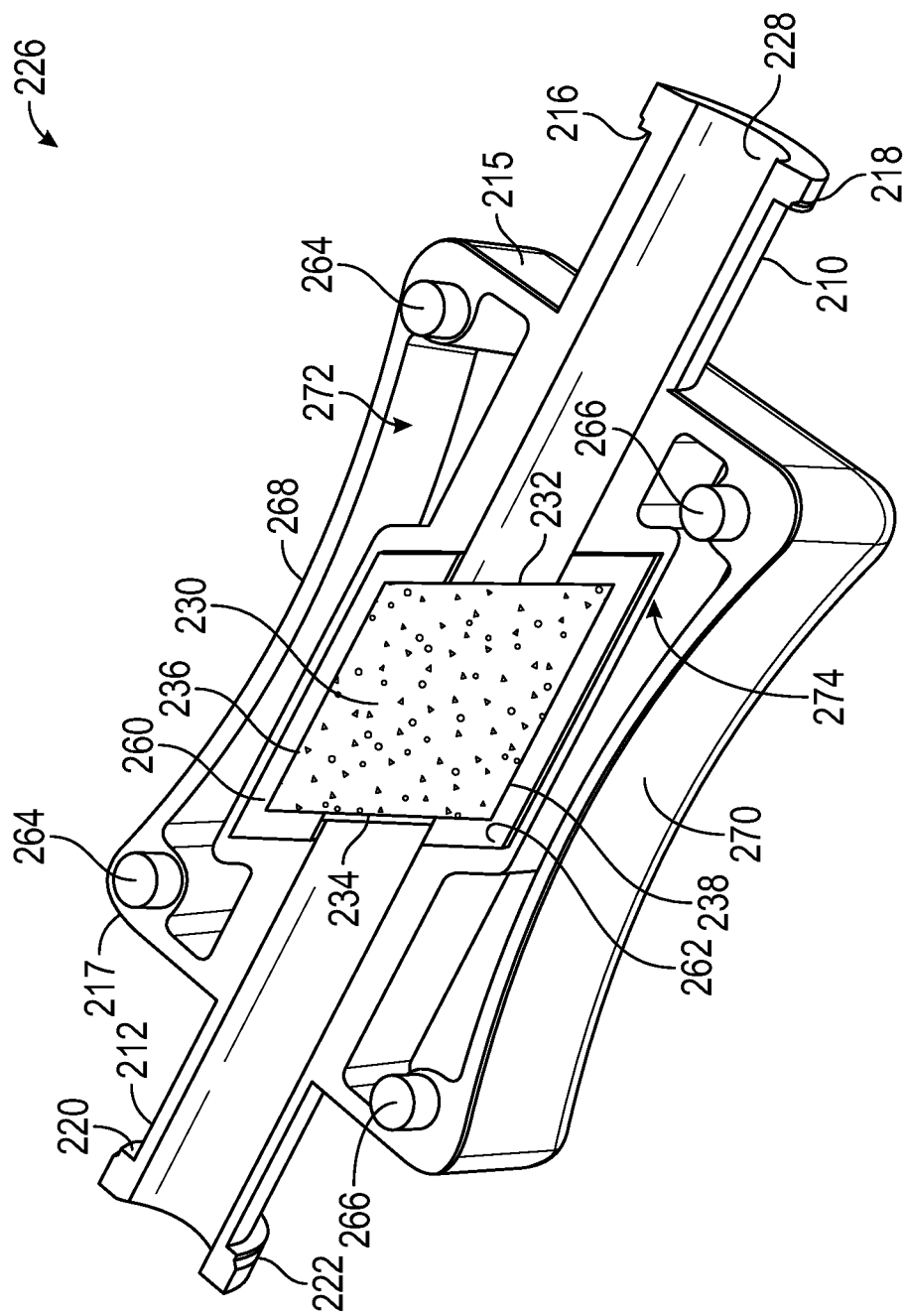
FIG. 12 is another cross-sectional view of the embodiment of FIG. 10, illustrating a second housing section thereof.

With reference to FIGS. 10-12, morselizer 200 is comprised of first end section 210, second end section 212, and housing 214 juxtaposed between first end section 210 and second end section 212. First end section 210 comprises a cylindrically-shaped member extending from a first sidewall section 215 of the housing 214. Second end section 212 comprises a cylindrically-shaped member extending from a second sidewall section 217 of the housing 214 opposite the first sidewall section 215. A channel 228, which extends axially between first end section 210 and second end section 212 and through housing 214, provides an axial liquid pathway through morselizer 200. Preferably, the inner diameter of channel 228 is axially continuous, with the inner diameters of each of first end section 210, second end section 212, and channel 228 the same. Channel 228 of morselizer 200 can have an inner diameter of any size capable of being complementarily sized to structures with small-scale liquid fittings, preferably in the range of 0.1 mm to 10 mm, more preferably in the range of 2 to 5 mm, most preferably in the range of 3 to 4 mm.

With reference to FIGS. 10-12, each end section 210/212 of morselizer 200 comprises an axially and radially hollow luer fitting that is attachable to a structure with a complementarily sized luer fitting. First end section 210 can further include an outwardly extending shoulder 216 and second end section 212 can further include an outwardly extending shoulder 220. The attachment of the morselizer 200 at each of the end sections 210 and 212 comprising a luer fitting to a structure containing a substantially liquid solution with substantially solid materials suspended therein and having a complementarily sized luer fitting prevents any solution leakage out of the structure during material flow from the structure to morselizer 200. The structure with a complementarily sized luer fitting and attachable to the morselizer 200 at each of the end sections 210/212 can comprise any structure with a luer fitting or luer-compatible fitting (such as a non-luer fitting to luer fitting adapter or other luer to non-luer adaptive structure), such as laboratory glassware, plasticware, or metalware, including, by way of example, only and not of limitation, vials, tubes (boiling, test, Thiele), luer lock tip or luer slip tip syringes, burettes, pipettes, cylinders, flasks, beakers, funnels, distilling columns, chromatography columns or other columns used in analytical techniques, or condensers.

The luer fittings comprising end sections 210/212 can be characterized as either (i) "male", with the luer fitting on end section 210/212 of morselizer 200 accommodated within another structure with a luer fitting when the structure is attached to the morselizer 200; or (ii) "female", with the luer fitting on end section 210/212 of morselizer 200 accommodating there another structure with a luer fitting when the structure is attached to the morselizer 200. Moreover, morselizer end section 210/212 comprising a luer fitting can be threaded or unthreaded, with such threaded or unthreaded morselizer end section 210/212 attachable to a complementarily sized unthreaded or threaded luer fitting on a structure, with (i) the threaded mating and frictional forces generated between the structure and morselizer 200 maintaining the attachment of a threaded morselizer end section 210/212 to a threaded structure and (ii) frictional forces alone maintaining the morselizer-structure attachment in the absence of a mating of threads between the morselizer end section 210/212 and the structure fitting. By way of example only and not of limitation, in an embodiment of the invention, shoulder 216 of morselizer end section 210 can include threading 218 and shoulder 220 of morselizer end section 212 can include threading 222, to allow for a threaded attachment of the end section 210/212 of morselizer 200 to a structure with a complementarily sized threaded luer fitting. Threading 218/222 can comprise various threading, such, as a single thread, double thread, triple thread, or more threads, as may be needed for attaching morselizer 200 to a given structure with a complementarily sized threaded luer fitting. In other embodiments (not depicted) threading may be formed on an inner wall (female), or both outer and inner walls (male-female) of morselizer end section 210/212 to allow for a threaded attachment of the end section 210/212 of morselizer 200 to a structure with a complementarily sized threaded luer fitting. In yet another embodiment of the invention, one or more of end sections 210/212 can comprise a threaded luer fitting that is attachable to a structure with a complementarily sized unthreaded luer fitting (not depicted) by pressing the morselizer 200 and structure together so as to form a luer slip attachment between the morselizer end section 210/212 and the structure luer fitting, with the attachment of a morselizer end section 210/212 comprising a threaded luer fitting to a complementarily sized unthreaded luer fitting on a structure effectuated from frictional forces generated between the structure and morselizer 200.

With reference to FIGS. 10-13, housing 214 of morselizer 200 can be divided into two main components: a first housing section 224 and a second housing section 226 which, when approximated, together form housing 214. With reference to FIGS. 10-11, first housing section 224 comprises a partially hollow structure defined by a first lateral sidewall 215, a posterior sidewall 252, a second lateral sidewall 217, an anterior sidewall 254, and a main wall 255. As seen in this embodiment, and with reference to FIG. 11, a portion of posterior sidewall 252 and a portion of anterior sidewall 254 can each have a substantially concave curvature. However, it should be understood that sidewalls 252/254 can be shaped differently, as desired By way of example only and not of limitation, sidewalls 252/254 could be flat or have a convex curvature, without departing from the spirit and scope of the invention.

Still referring to FIG. 11, first housing section 224 further includes a first longitudinal portion of channel 228 formed therethrough. Channel 228 is flanked by at least one blade support. Preferably, a plurality of spaced-apart blade supports 240 and 242 are provided, including a posterior blade support 240 and an anterior blade support 242. As seen in this embodiment, each blade support 240 and 242 can have a parallelogram shape, with adjacent internal angles thereof being supplementary and opposite internal angles thereof being equal. In this way, the spaced-apart blade supports 240 and 242, together, conform to the shape of a blade 230 (as seen in FIG. 12), as described further herein. However, it should be understood that blade supports 240 and 240 may take on other shapes as long as they conform to the shape of the blade 230, without departing from the spirit and scope of the invention.

Still referring to FIG. 11, first housing section 224 farther includes at least one depression region. Preferably, a plurality of depression regions 244 and 246 are provided, including a posterior depression region 244 and an anterior depression region 246. As seen in this embodiment, each depression region 244/246 can be three-sided, extending from a first portion of channel 228 proximal first end section 210, continuing alongside blade support 240/242, and terminating at a second portion of channel 228 proximal second end section 212. Each depression region 244/246 is configured to receive a portion of a retaining wall 260/262 (shown in FIG. 12) therein when first housing section 224 and second housing section 226 are approximated, as further described herein.

Still referring to FIG. 11, first housing section 224 further includes at least one receptacle. Preferably, a plurality of receptacles are provided, including at least one posterior receptacle 248 and at least one anterior receptacle 250. In this embodiment, two posterior receptacles 248 and two anterior receptacles 250 are provided, for a total of four receptacles. However, it should be understood that more than four or less than four receptacles may be provided, without departing from the spirit and scope of the invention. Each receptacle 248/250 includes a circular-shaped opening and is configured to receive one of a plurality of pegs 264 or 266 (shown in FIG. 12) when first housing section 224 and second housing section 226 are approximated, as further described herein. Each receptacle 248/250 can be positioned proximal one of each of four corners of first housing section 224. While in this embodiment receptacles 248/250 are shown as being circular-shaped, it should be understood that receptacles 248/250 may take on other shapes, without departing from the spirit and scope of the invention.

Still referring to FIG. 11, first housing section 224 further includes cavities 256 and 258, including a posterior cavity 256 and an anterior cavity 258. The cavities 256 and 258 are longitudinally spaced-apart from one another, with posterior cavity 256 formed alongside a first side of channel 228 and anterior cavity 258 formed alongside a second side of channel 228.

With reference to FIGS. 10 and 12, second housing section 226 comprises a partially hollow structure defined by a first lateral sidewall 215, a posterior sidewall 268, a second lateral sidewall 217, an anterior sidewall 270, and a main wall 271. As seen in this embodiment, and with reference to FIG. 12, a portion of posterior sidewall 268 and a portion of anterior sidewall 270 can each have a substantially concave curvature. However, it should be understood that sidewalk 268/270 can be shaped differently, as desired. By way of example only and not of limitation, sidewalk 268/270 could be flat or have a convex curvature, without departing from the spirit and scope of the invention. As can be seen from a review of FIGS. 11-12, each sidewall 268/270 is a mirror image of each sidewall 252/254, respectively.

With reference to FIG. 12, second housing section 226 further includes a second longitudinal portion of channel 228 formed therethrough. As can be seen from a review of FIGS. 11-12, second longitudinal portion of channel 228 comprises a mirror image of first longitudinal portion of channel 228 that runs through first housing, section 224. In second housing section 226, channel 228 is flanked by at, least one blade support positioned beneath a blade 230. Preferably, a plurality of blade supports are provided, including a posterior blade support that is a mirror image of posterior blade support 240 of first housing section 224 and an anterior blade support that is a mirror image of anterior blade support 242 of first housing section 224.

Still referring to FIG. 12, second housing section 226 further includes at least one retaining wall. Preferably, a plurality of retaining walls 260 and 262 are provided, including a posterior, retaining wall 260 and an anterior retaining wall 262. As seen in this embodiment, each retaining wall 260/262 can be three-sided, extending from, a first portion of channel 228 proximal first end section 210, continuing longitudinally alongside blade 230, and terminating at a second portion of channel 228 proximal second end section 212. An outer portion of each retaining wall 260/262 is configured to be positioned within depression region 244/246, respectively (shown in FIG. 11), and to hold blade 230 in position within the housing 214 when first housing section 224 and second housing section 226 are approximated.

Still referring to FIG. 12, second housing section 226 further includes at least one peg. Preferably, a plurality of pegs are provided, including at least one posterior peg 264 and at least one anterior peg 266. In this embodiment, two posterior pegs 264 and two anterior pegs 266 are provided, for a total of four pegs. However, it should be understood that more than four or less than four pegs may be provided, as long, as the number of pegs 264/266 corresponds to the number of receptacles 248/250, respectively, without departing from the spirit and scope of the invention. As seen in this embodiment, each peg 264/266 is cylindrically-shaped and is configured to be positioned in one of a plurality of receptacles 248/250 (shown in FIG. 11), respectively, when first housing section 224 and second housing section 226 are approximated. Thus, when pegs 264/266 of second housing section 226 are positioned in receptacles 248/250, respectively, of first housing section 224, first housing section 224 and second housing section 226 can be securely coupled together to form housing 214. Each peg 264/266 can be positioned proximal one of each of four corners of second housing section 226. While in this embodiment pegs 264/266 are shown as being cylindrically-shaped, it should be understood that pegs 264/266 may take on other shapes as long as they correspond with the shape of receptacles 248/250, without departing the spirit and scope of the invention.

Still referring to FIG. 12, second housing section 226 further includes cavities 272 and 274, including a posterior cavity 272 and an anterior cavity 274. The cavities 272 and 274 are longitudinally spaced-apart from one another, with posterior cavity 272 formed alongside a first side of channel 228 and anterior cavity 274 formed alongside a second side of channel 228. As can be seen from a review of FIGS. 11-12, each cavity 272/274 is a mirror image of each cavity 256/258 respectively.

Figure 13:
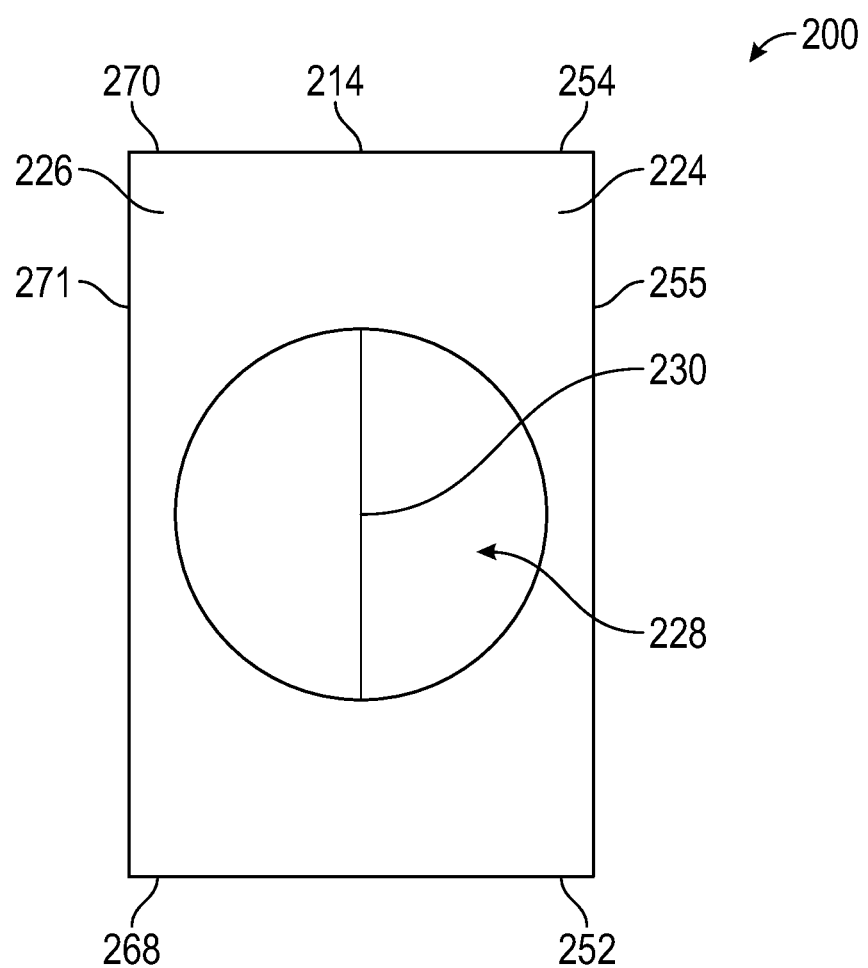
FIG. 13 is a cross-sectional end view of the embodiment of FIG. 10.

With reference to FIGS. 11-13, disposed within housing 214 is one or more blades 230, preferably one blade 230. With reference to FIG. 12, each of the one or more blades 230 is a planar structure defined by posterior and anterior ends and at least two side ends wherein at least, two ends, preferably the two side ends, comprise cutting ends, such blade 230 comprising (i) first end 232 proximal first end section 210 and preferably comprising a cutting end, (ii) a posterior end 236 positioned to abut posterior retaining wall 260 of second housing section 226, (iii) a second end 234 proximal second end section 212 and preferably comprising a cutting end, and (iv) an anterior end 238 positioned to abut anterior retaining wall 262 of second housing section 226. Such one or more blades 230 extends transversally from the blade posterior end 236 at a first position abutting posterior retaining, wall 260 across the inner diameter of channel 228 to the blade anterior end 238 at a second position abutting anterior retaining wall 262 opposite the first position. Thus, the one or more blades 230 is configured to be positioned between the posterior retaining wall 260 and the anterior retaining wall 262. While in this embodiment, blade 230 is shown as being substantially parallelogram-shaped with adjacent internal angles thereof being supplementary and opposite internal angles thereof being equal, it should be understood that blade 230 can be shaped differently, as desired. By way of example only and not of limitation, blade 230 could be substantially square-shaped, rectangular-shaped, or the like, without departing from the spirit and scope of the invention.

Each of the one or more blades 230 positioned within housing 214 comprises any blade type known in the art. Preferably, at least one of the one or more blades 230 comprises a scalpel blade, more preferably, a double-sided scalpel blade 230 with first end 232 proximal first end section 210 and second end 234 proximal second end section 212 wherein first end 232 and second end 234 each extend transversally across channel 228 in parallel with one another.

In a preferred embodiment, the morselizer 200 can be assembled by first positioning the blade 230 in the second housing section 226, such that blade 230 rests on blade supports and is positioned between retaining walls 260 and 262 (see FIG. 12). In this way, blade 230 can be accurately centered in the second housing section 226. Next, the two housing sections 224 and 226 would be approximated (see FIG. 10). When the two housing sections 224 and 226 are approximated, retaining walls 260/262 will be positioned within depression regions 244/246, respectively, and pegs 264/266 will be positioned within receptacles 248/250, respectively. When approximated, first housing section 224 and second housing section 226 form housing 214 of morselizer 200, having complete channel 228 running therethrough. With blade 230 being positioned between retaining walls 260 and 262 of second housing section 226 and retaining walls 260/262, in turn, being positioned in depression regions 244/246 of the first housing section 224 when the two housing sections 224 and 226 are approximated, this ensures accurate centering of blade 230 within the channel 228 of morselizer 200.

The morselizer 200 allows for atraumatic resizing of material through axial liquid transfer through channel 228 of morselizer 200 by (I) attaching a first structure with a luer fitting containing material in a liquid solution to the morselizer 200 by attaching the first structure luer fitting to the morselizer 200 luer fitting, at the first end section 210 of the morselizer 200 and attaching a second structure with a luer fitting to the morselizer 200 luer fitting at the second end 212 of the morselizer 200; and (II) transferring material in the liquid solution from the first structure to the morselizer 200 through the first structure-morselizer luer fitting attachment, thence through the channel 228 of the morselizer 200, where material is resized by the one or more blades 230 positioned in the morselizer housing 214 and through the second end section 212 of the morselizer 200 to the second structure through the second structure-morselizer bier fitting attachment; and, as needed or desired by the user depending on the give size of the diameter and the desired size of the diameter, (III) successively transferring material in the liquid solution from the second structure through the morselizer 200 to the first structure and thence back to the second structure through the morselizer 200 as discussed above at (II). Once the material has been atraumatically resized in this manner, the resized material will be suitable for injection such as through a fine needle, for example.

Although the description above contains much specificity, such description specificity should not be construed as limiting the scope of the embodiments of the invention but as merely providing illustrations of some of the presently-preferred embodiments. Thus, the scope of the invention should be determined by the appended claims and their legal equivalents, rather than by the examples given.

I claim:

1. A morselizer comprising, in combination:
   a first end section, wherein the first end section comprises an axially and radially hollow luer fitting that is attachable to a structure with a complimentarily sized luer fitting;
   a second end section, wherein the second end section comprises an axially and radially hollow luer fitting that is attachable to a structure with a complimentarily sized leer fitting;
   a housing juxtaposed between the first end section and the second end section, wherein the housing comprises a first housing section and a section housing section, wherein the first housing section and second housing section are configured to be coupled together to form the housing;
   a channel extending axially between the first end section and the second end section and through the housing providing an axial liquid pathway therein; and
   at least one blade disposed within the housing and extending transversally across an inner diameter of the channel, wherein the at least one blade comprises a plurality of ends, including a posterior end, an anterior end, and at least two side ends, wherein the at least two side ends comprise cutting ends.

2. The morselizer of claim 1, wherein the first end section further comprises a shoulder, the shoulder including threading thereon.

3. The morselizer of claim 1, wherein the second end section further comprises a shoulder, the shoulder including threading thereon.

4. The morselizer of claim 1, wherein the first housing section comprises at least one blade support.

5. The morselizer of claim 1, wherein the second housing section comprises at least one blade support.

6. The morselizer of claim 1, wherein the first housing section comprises at least one depression region and the second housing section comprises at least one retaining wall, wherein the at least one depression region is configured to receive a portion of the at least one retaining wall therein when the first housing section and second housing section are coupled.

7. The morselizer of claim 6, wherein the first housing section comprises two depression regions, including an anterior depression region and a posterior depression region, and the second housing section comprises two retaining walls, including an anterior retaining wall and a posterior retaining wall.

8. The morselizer of claim 7, wherein the blade is configured to be positioned between the anterior retaining wall and the posterior retaining wall.

9. The morselizer of claim 1, wherein the first housing section comprises at least one receptacle and the second housing section comprises at least one peg, wherein the at least one receptacle is configured to receive the at least one peg therein when the first housing section and second housing section are coupled.

10. The morselizer of claim 1, wherein the at least one blade has a parallelogram shape, wherein adjacent internal angles thereof are supplementary and opposite internal angles thereof are equal.

11. A morselizer comprising, in combination:
    a first end section, wherein the first end section comprises an axially and radially hollow luer fitting that is attachable to a structure with a complimentarily sized luer fitting;

wherein the first end section comprises a shoulder, the shoulder including threading thereon;
a second end section, wherein the second end section comprises an axially and radially hollow luer fitting that is attachable to a structure with a complimentarily sized luer fitting;
wherein the second end section comprises a shoulder, the shoulder including threading thereon;
a housing juxtaposed between the first end section and the second end section, wherein the housing comprises a first housing section a section housing section, wherein the first housing section and second housing section are configured to be coupled together to form the housing;
wherein the first housing section and the second housing section each include at least one blade support;
a channel extending axially between the first end section and the second end section and through the housing providing an axial liquid pathway therein; and
at least one blade disposed within the housing and extending transversally across an inner diameter of the channel, wherein the at least one blade comprises a plurality of ends, including a posterior end, an anterior end, and at least two side ends, wherein the at least two side ends comprise cutting ends.

12. The morselizer of claim 11, wherein the first housing section further comprises two blade supports, including an anterior blade support and a posterior blade support.

13. The morselizer of claim 11, wherein the first housing section further comprises at least one depression region and the second housing section further comprises at least one retaining wall, wherein the at least one depression region is configured to receive a portion of the at least one retaining wall therein when the first housing section and second housing section are coupled.

14. The morselizer of claim 13, wherein the first housing section comprises two depression regions, including an anterior depression region and a posterior depression region, and the second housing section comprises two retaining walls, including an anterior retaining wall and a posterior retaining wall.

15. The morselizer of claim 14, wherein the blade is configured to be positioned between the anterior retaining wall and the posterior retaining wall.

16. The morselizer of claim 11, wherein the first housing section further comprises at least one receptacle and the second housing section further comprises at least one peg, wherein the at least one receptacle is configured to receive the at least one peg therein when the first housing section and second housing section are coupled.

17. The morselizer of claim 11, wherein the at least one blade has a parallelogram shape, wherein adjacent internal angles thereof are supplementary and opposite internal angles thereof are equal.

18. A morselizer comprising, in combination:
a first end section, wherein the first end section comprises an axially and radially hollow luer fitting that is attachable to a structure with a complimentarily sized luer fitting;
wherein the first end section comprises a shoulder, the shoulder including threading thereon;
a second end section, wherein the second end section comprises an axially and radially hollow luer fitting that is attachable to a structure with a complimentarily sized luer fitting;
wherein the second end section comprises a shoulder, the shoulder including threading thereon;
a housing juxtaposed between the first end section and the second end section, wherein the housing comprises:
a first housing section, wherein the first housing section comprises at least one depression region and at least one receptacle; and
a section housing section, wherein the second housing comprises at least one retaining wall and at least one peg;
wherein the first housing section and second housing section are configured to be coupled together to form the housing, wherein the at least one depression region is configured to receive a portion of the at least one retaining wall and the at least one receptacle is configured to receive the at least one peg;
wherein the first housing section and the second housing section each include at least one blade support;
a channel extending axially between the first end section and the second end section and through the housing providing an axial liquid pathway therein; and
at least one blade disposed within the housing and extending transversally across an inner diameter or the channel, wherein the at least one blade comprises a plurality of ends, including a posterior end, an anterior end, and at least two side ends, wherein the at least two side ends comprise cutting ends.

19. The morselizer of claim 18, wherein the first housing section further comprises two blade supports, including an anterior blade support and a posterior blade support.

20. The morselizer of claim 18, wherein the first housing section comprises two depression regions, including an anterior depression region and a posterior depression region, and the second housing section comprises two retaining walls, including an anterior retaining wall and a posterior retaining wall;
wherein the blade is configured to be positioned between the anterior retaining wall and the posterior retaining wall.

* * * * *